US008894599B2

(12) United States Patent  
Kataria

(10) Patent No.: US 8,894,599 B2
(45) Date of Patent: Nov. 25, 2014

(54) UTERINE STIMULANT STICKS

(76) Inventor: Om Kataria, Sonepat Haryana (IN)

( * ) Notice: Subject to any disclaimer, the term of this patent is extended or adjusted under 35 U.S.C. 154(b) by 451 days.

(21) Appl. No.: 12/530,585

(22) PCT Filed: Sep. 12, 2007

(86) PCT No.: PCT/IN2007/000409
§ 371 (c)(1),
(2), (4) Date: Sep. 9, 2009

(87) PCT Pub. No.: WO2008/111090
PCT Pub. Date: Sep. 18, 2008

(65) Prior Publication Data
US 2010/0100035 A1    Apr. 22, 2010

(30) Foreign Application Priority Data
Mar. 15, 2007    (IN) .............................. 569/DEL/2007

(51) Int. Cl.
*A61M 35/00*    (2006.01)
*A61K 33/34*    (2006.01)
*A61K 35/04*    (2006.01)
*A61K 36/49*    (2006.01)

(52) U.S. Cl.
CPC ................. *A61K 36/49* (2013.01); *A61K 33/34* (2013.01); *A61K 35/04* (2013.01)
USPC .......................................................... 604/1

(58) Field of Classification Search
CPC ............ A61F 13/38; A61F 2250/0067; A61B 2010/0074
USPC .......................................................... 604/1
See application file for complete search history.

(56) References Cited

U.S. PATENT DOCUMENTS

| | | | |
|---|---|---|---|
| 3,664,341 A * | 5/1972 | Gordon .......................... | 604/288 |
| 5,646,178 A | 7/1997 | Walker et al. | |
| 6,467,982 B1 * | 10/2002 | Tsao .............................. | 401/263 |
| 6,667,026 B1 | 12/2003 | Goldman | |
| 2003/0059488 A1 | 3/2003 | Daniels | |
| 2005/0256440 A1 * | 11/2005 | Zunker et al. ..................... | 604/1 |
| 2005/0267395 A1 * | 12/2005 | Mangold et al. .................. | 604/1 |

FOREIGN PATENT DOCUMENTS

| | | |
|---|---|---|
| EP | 0955051 A | 11/1999 |
| FR | 2772604 A | 6/1999 |
| RU | 2036643 C1 | 6/1995 |

(Continued)

OTHER PUBLICATIONS

Kuo, M "*Lactarius*: The Milky Caps" Internet Citation [Online] Jul. 2007, pp. 1-9; XP002461330 Retrieved from the Internet: URL: http://www.mushroomexpert.com/lactarius.html.

(Continued)

*Primary Examiner* — Kevin C Sirmons
*Assistant Examiner* — Deanna K Hall
(74) *Attorney, Agent, or Firm* — Volpe and Koenig, P.C.

(57) ABSTRACT

The invention discloses a novel uterine stimulant, which is in the form of the stick. The uterine stimulation stick, on administration, helps a woman's uterus to contract, or to increase the frequency and intensity of the contractions. Such medicine can be suitably used to induce (start) or augment (speed) labor; facilitate uterine contractions following a miscarriage; induce abortion; or reduce hemorrhage following childbirth or abortion. The proposed medicine produces normal result for desired purpose, without any significant side effect for the mother or fetus.

7 Claims, 4 Drawing Sheets

(56) References Cited

FOREIGN PATENT DOCUMENTS

| RU | 2065747 C1 | 8/1996 |
| --- | --- | --- |
| RU | 2092173 C1 | 10/1997 |
| RU | 2097028 C1 | 11/1997 |
| RU | 2108784 C1 | 4/1998 |
| RU | 2132184 C1 | 6/1999 |
| SU | 1412049 A | 9/1990 |
| WO | 9411010 A | 5/1994 |
| ZA | 200308879 A | 7/2004 |

OTHER PUBLICATIONS

Sterner Olov et al. "Toxic terpenoids isolated from higher fungi"; XP002461333; Czech Mycology vol. 48, No. 1, 1 page, 1995 (Abstract only).

Das Kanad et al. "*Lactarius* in Kumaon Himalaya 3: A New Species of Subgenus Lactifluus," Mycotaxon 90, 2 (Oct.-Dec. 2004):285-289 (Abstract).

Vrinda KR et al. "*Lactarius* ignifluus (Russulaceae), A New Species from India," *Persoonia*, 18 (1): 129 (2002) (Abstract).

De Bernardi M et al. "The Chemistry of *Lactarius fuliginosus* and *Lactarius picinus*," Tetrahedron, v. 48 (35): 7331-7344, XP 002461331 (1992).

Wikipedia: Ammonium bituminosulfonate Internet Citation [online] Aug. 2007 (Aug. 11, 2007), 4 pages, XP002461332 Retrieved from the Internet: URL: http:/en.wikipedia.org.wiki/Ichthamol.

Tamang, Anand "Induced Abortions and Subsequent Reproductive Behaviour Among Women in Urban Areas of Nepal," Social Change, 26(3&4), pp. 271-285 (Sep.-Dec. 1996). URL:http://www.womenstudies.in/elib/contr_practice/ab_induced_abortions.pdf [Retieved on Jul. 7, 2014].

Agarwal, Rachna, MD et al. "Gangrene of the Uterus: A Dreaded Complication of Unsafe Abortions", The Female Patient, vol. 32, pp. 45-50 (Oct. 1, 2007). URL:http://www.cutis.com/fileadmin/qhi_archive/ArticlePDF/TFP/032100045.pdf [Retrieved on Jul. 7, 2014].

Bhosale P B et al. "An unusual case of hip disability—(a case report)"; Journal of Postgraduate Medicine, XP055100764; pp. 232-234, Jan. 1, 1989. URL:http://jpgmonline.com/printarticle.asp?issn=0022-3859;year=1989;volume=34;issue=4;spage=232;epage=4;aulast=Bhosale [Retrieved Jul. 7, 2014].

\* cited by examiner

UTERINE STIMULANT STICKS

1. INTRODUCTION

The present invention is related with a medicine, in the form of a stick, for starting uterine contraction in normal way. The proposed stick is absorbed with an active medicine composition containing a particular ratio of Icthomal, Oak milk and Blue Vitriol. Along with this uterine stimulant stick, the method of its application is also novel and needs patent protection.

1.1. Background of the Invention

Uterine stimulants are used to induce, or begin, labor in certain circumstances when the mother's labor has not started naturally. These circumstances may include the mother's being past her due date; that is, the pregnancy has lasted longer than 40 weeks. Labor is especially likely to be induced if tests indicate a decrease in the volume of amniotic fluid. Uterine stimulants may also be used in cases of premature rupture of the membranes; preeclampsia (elevated blood pressure in the later stages of pregnancy); diabetes; and intrauterine growth retardation (IUGR), if these conditions require delivery before labor has begun. These medications may be recommended if the expectant mother lives a great distance from the healthcare facility and there is concern for either her or her baby's safety if she were unable to reach the facility once labor begins. Uterine stimulants are also used in the augmentation of existing contractions, to increase their strength and frequency when labor is not progressing well.

According to the American College of Obstetrics and Gynecology (ACOG), the 1990's saw an increase in the rate of induced labor—from 9% of deliveries to 18%. The ACOG reported in May 2001 that the increase in the rate of Caesarian sections seen over the same period of time was not due to the induction process but to such other factors as the condition of the mother's cervix at the time of induction and whether the pregnancy was the woman's first.

1.2. Prior Art Related to the Uterine Stimulants

The three uterine stimulants used most frequently are the oxytocins, prostaglandins, and ergot alkaloids. Uterine stimulants may be given intravenously (IV), intramuscularly (IM), as a vaginal gel or suppository, or by mouth.

Oxytocin is a naturally occurring, hormone used to induce labor. The production and secretion of natural oxytocin is stimulated by the pituitary gland. It is also available in synthetic form under the trade names of Pitocin and Syntocinon. Oxytocin is used in a contraction stress test (CST). A CST is done prior to the onset of labor to evaluate the fetus's ability to withstand the contractions of the uterus. Oxytocin may be used in the treatment of a miscarriage to assure that all the products of conception (POC) are expelled from the uterus. In a routine delivery, oxytocin may be given to the mother after the placenta has been delivered in order to help the uterus contract and minimize bleeding. It is also used to treat uterine hemorrhage.

Prostaglandins (PGs) play a major role in stimulating the uterine contractions at the beginning of labor. Research indicates that PGs are also involved in the transition from, the early phase of labor to the later stages. In addition, PGs may be used to ripen the cervix prior to induction. Administration of prostaglandin is sometimes sufficient to stimulate labor, and the woman needs no further medication for labor to progress.

Ergot alkaloids are derived from a fungus, *Claviceps purpurea*, which grows primarily on rye grain. The fungus forms a hard blackish body known as a sclerotium, which contains alkaloid compounds that can be used to treat migraine headache. Ergot by itself, however, is toxic to the central nervous system of humans and animals, producing irritability, spasms, cramps, and convulsions. Because of its potentially harmful side effects, one ergot-based drug (Ergonovine or Ergotrate) was taken off the American market in 1993. Methylergonovine maleate (Methergine) is now the only ergot derivative in use in the United States. It is given only as a uterine stimulant to control PPH. Because of the risk of complications, and because the use of Methergine is contraindicated in many women, it has largely been replaced by the PGs as a second-line uterine stimulants.

Though several uterine stimulants are available in market, but all of them have one or more considerable side-effect(s), depending upon the condition of patient and on the dose/duration of such medicine(s) applied.

Oxytocin takes effect rapidly when it is given intravenously. Individual responses to oxytocin vary considerably; for this reason, the drug dosage is usually increased slowly and incrementally. Oxytocin can cause hyperstimulation of the uterus, which in turn can place the fetus at risk for asphyxia uterine rupture has also been linked to oxytocin administration. Oxytocin has a mild antidiuretic effect that is usually dose-related; it can lead to water intoxication (hyponatremia). Onset occurs gradually and may go unnoticed. Signs of water intoxication may include reduced urine output, confusion, nausea, convulsions, and coma. Expectant mothers receiving oxytocin should have their blood pressure monitored closely, as both hypotension and hypertension can occur. Although the subject remains controversial, some evidence suggests oxytocin increases the incidence of neonatal jaundice. Although oxytocin may increase the risk of uterine rupture in women who were delivered by Caesarian section in a previous pregnancy, contraindications to the use of the drug are virtually the same as contraindications for labor. Other side effects of oxytocin include nausea, vomiting, cardiac arrhythmias, and fetal bradycardia (slowing of the heartbeat).

Significant systemic side effects, are associated with the use of Prostaglandins (PGs). These include headache, nausea, diarrhea, tachycardia, vomiting, chills, fever, sweating, hypertension, and hypotension. There is also increased incidence of uterine hyperstimulation and potential for uterine rupture. PGF2 alpha (carboprost—Prostin 15-M or Hemabate) can cause hypotension, pulmonary edema, and—in women with asthma—intense bronchospasms. Because it stimulates the production of steroids, carboprost may be contraindicated in women with adrenal gland disease. When used for abortion it may result in sufficient blood loss to cause anemia, necessitating a transfusion. Medical problems (or history) of diabetes, epilepsy, heart or blood vessel disease, jaundice, kidney disease, or liver disease should be brought to the attention of the health care practitioner before the use of carboprost. Also, in rare instances, ophthalmic pressure has increased in women with glaucoma with the use of this PG.

Ergots have an alpha-adrenergic action with a vasoconstricive effect. They can cause hypertension, cardiovascular changes, cyanosis, muscle pain, tingling, other symptoms associated with decreased blood circulation, and severe uterine cramping.

Therefore the medical community is in search for an ideal uterine stimulant, which can provide contraction in normal way without any significant side effect. The proposed uterine stimulant stick and its method of administration, are unique, and novel. This medicine not only starts contraction in normal way but also does not show side effects except mild temperature and vomiting in less than 2% cases. Uterine stimulant sticks are very much applicable in cases like intra uterine death, mal-formed baby, poor contraction, hydatid mole and to avoid C-section.

2. SUMMARY OF THE INVENTION

Uterine stimulants (uterotonics) are medications given to cause a woman's uterus to contract, or to increase the frequency and intensity of the contractions. These drugs are used to induce (start) or augment (speed) labor; facilitate uterine contractions following a miscarriage; induce abortion; or reduce hemorrhage following childbirth or abortion. Uterotonics may be given intravenously (IV), intramuscularly (IM), as a vaginal gel or suppository, or by mouth.

2.1. The Proposed Medicine and its Method of Administration are Unique and Novel.

Proposed uterine stimulant is in the form of stick, shocked with active medicine. The uterine stimulant stick is poured with certain softening agent like soft paraffin (or other inert cream gel). Then this stick, at least one in number, is inserted into the gravid uterus with the help of the dilator and the stick starts showing its effect normally not before 8-10 hours. One stick is sufficient in normal delivery, but in other abnormal cases two sticks are necessary. In certain uterine complications (like in the case of abortion after 4-5 months pregnancy) three sticks may be applied. But in some rear cases the proposed stick gives desired outcome within 2-3 hours. It initiates labour pain and provide normal contraction to the gravid uterus to help its dilution. Once labour pain starts and the uterus gets one-fourth dilution, the stick is removed so that the delivery, similar as a normal delivery, can occur and the uterus can gets complete evacuation. In other than normal delivery cases, the stick is left in the uterus for its prolonged action, until the delivery takes place. Actually in normal cases, the stick performs its action in short duration, but in abnormal cases, it requires long duration. In cases other than delivery of normal baby, there is no fear of harm to the dead fetus/baby due to presence of uterine stimulant stick. In such cases, stick finally comes out of uterus by itself. In some cases these uterine stimulant sticks show their effect after 20-24 hours (for example in case of thick wall of uterus).

It is more convenient to increase the concentration of the medicine in single stick, rather applying two or three sticks. Application of single uterine stimulant stick with high medicine content or more than one sticks with mild medicine concentration—such matters depends on the condition of the peasant, seriousness of the uterine complication and at the same time the discretion of the doctor.

The proposed uterine stimulant stick and the method of its application help in avoiding any risk of the life of the mother/patient and of the child. Apart from this, the proposed medicine and the method reduce the possibility of any delivery by Caesarian section.

3. DETAIL DESCRIPTION OF THE INVENTION

The present, invention is associated with (i) preparation of the active medicine; (ii) preparation of uterine stimulant stick; (iii) method of application of these sticks; (iv) precautions in the application of these sticks; (v) side-effects. All these points are substantially described here.

Figure 1:
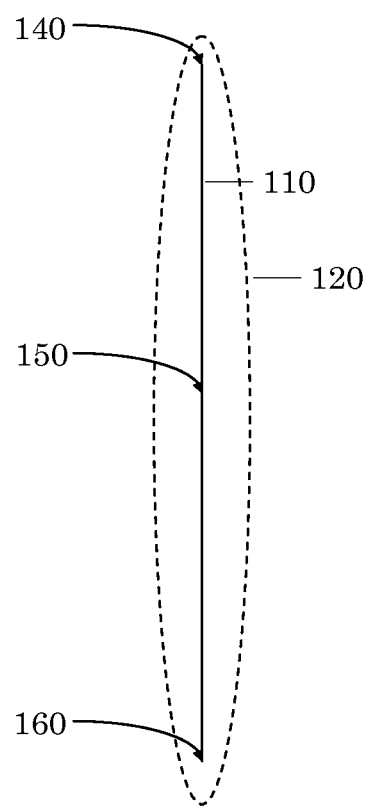
FIG. 1 illustrates a uterine stimulant stick.
Figure 2:
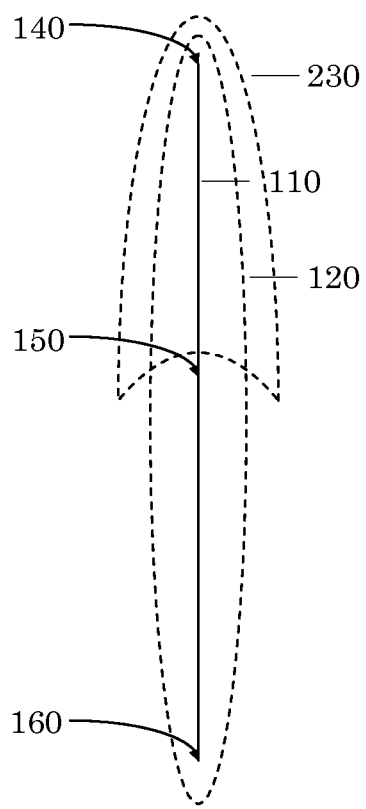
FIG. 2 illustrates a uterine stimulant stick.
Figure 3:
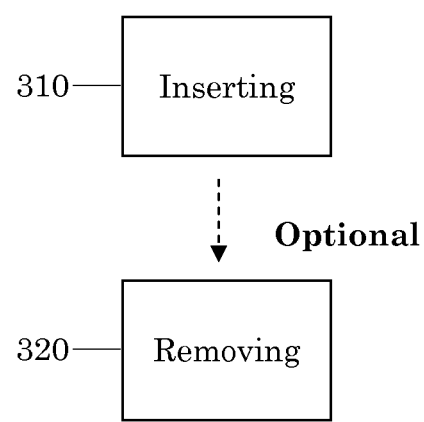
FIG. 3 illustrates a method of stimulating uterine contraction.
Figure 4:
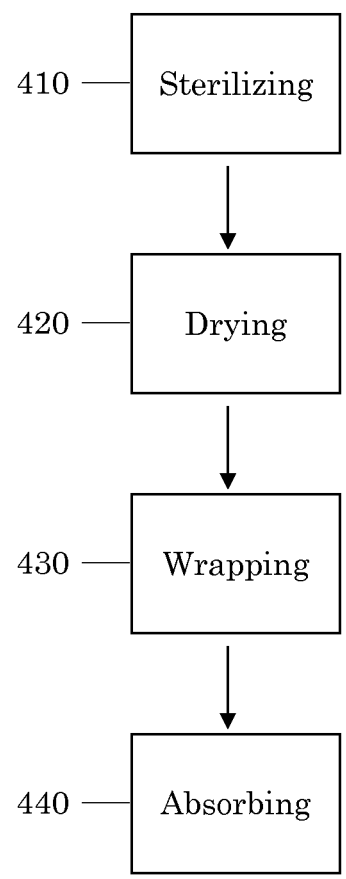
FIG. 4 illustrates a method of preparing a uterine stimulant stick.

Referring to FIG. 1, a uterine stimulant stick 110 is illustrated comprising a first end 140, a second end 160, a middle 150, and a first layer of absorbent material 120. Referring to FIG. 2, a uterine stimulant stick 110 is illustrated having a first end 140, a second end 160, a middle 150, a first layer of absorbent material 120, and a second layer of absorbent material 230. Referring to FIG. 3, a method of stimulating uterine contraction is illustrated comprising steps of inserting 310 at least one uterine stimulant stick inside the uterus of a patient, and optionally removing 320 the uterine stimulant stick. Referring to FIG. 4, a method of preparing a uterine stimulant stick is illustrated comprising steps of sterilizing 410 a round-surfaced inert stick to form a sterilized round-surfaced inert stick, drying 420 the sterilized round-surfaced inert stick to form a dried round-surfaced inert stick, wrapping 430 a first layer of absorbent material around a first end of the dried round-surfaced inert stick to form a wrapped round-surfaced inert stick, and absorbing 440 active uterine stimulant medicine on the wrapped round-surfaced inert stick to form the uterine stimulant stick.

3.1. Preparation of the Active Uterine Stimulant Medicine:

The medicine is a homogeneous mixture of three chemical compounds—Icthomal, Oak milk and powdered Blue vitriol. These three components are mixed together in a fixed ratio to prepare a thick and very viscous homogeneous solution. The ratio of these compounds can be varied to prepare medicine of different powers (strength). For example, Icthomal, Oak milk and Blue vitriol can be taken in the ratio 50:50:1 as standard composition (that is 500 mg:500 mg:10 mg respectively per stick). For normal delivery cases, low power medicines is sufficient, while in other abnormal and/or sever uterine complications stick(s) with variable high power medicine content can be applied.

3.2. Preparation of Uterine Stimulant Stick:

Before the preparation of the active stimulant medicine, thin and very smooth bamboo sticks with round surface are prepared. These round bamboo sticks are of about 10 cm length, which are boiled in pure drinking/distilled water for about 2-3 hours followed by drying in direct sun light. This prolong boiling of thin bamboo sticks is only to sterilize them. The sterilization and drying of these bamboo sticks can be carried out by any of the known modern methods. On the sterilized and dry bamboo stick a thin layer of clean and dry cotton is wrapped very tightly through out its round surface length. The Round surface of the stick supports the tight wrapping of the cotton layer. Tight wrapping of cotton is necessary to avoid loss/leakage of medicine from the stick or any other problem in handling the stick at the time of its application. This thin cotton layer, tightly wrapped on the stick absorbs the active uterine stimulant medicine and makes the stick surface smooth and safe in use. Even in spite of these bamboo sticks, any other naturally occurring material, wood or some synthetically prepared inert sticks can be utilized for wrapping up of cotton layer to shock the active medicine and for preparation of proposed uterine stimulant sticks. In present case sterilized thin and small bamboo sticks are selected for shocking active uterine stimulant medicine, as bamboo is easily available in Indian continent. For drying these bamboo sticks, more scientific and quicker methods may be adopted.

This cotton wrapped, sterilized and dry bamboo sticks are emerged in the thick viscous solution of active uterine stimulant medicine (up to about 8 cm) for about one minute. Finally these sticks are taken out of the bulk medicine solution and kept aside in air for about 4-6 hours, so that the sticks properly absorb the active medicine followed by their solidification. Again a second layer of medicine is made on the same sticks by again dipping them for second time in the same active medicine, followed by absorption and solidification of the medicine on sticks. When the active uterine stimulant medicine gets finally solidified on the cotton wrapped stick, a small piece of cotton is wrapped on that part of the stick which does not contain medicine—about 2 cm uncovered length of the stick. This portion of the stick, which is wrapped with only cotton and does not contain medicine, may be considered as a point to hold the stick safely. Finally the uterine stimulant sticks are ready for use.

3.3. Method of Application of Uterine Stimulant Sticks:

The method of application of proposed uterine stimulant stick(s) is new and different from other known conventional methods, that is intravenously (IV), intramuscularly (IM), as a vaginal gel or suppository, or by mouth. In the present method, the proposed uterine stimulant medicine is directly applied to the gravid uterus, with the help of thin, small, smooth, strong and inert stick(s). The uterine stimulation stick(s) is poured with certain softening agent like soft paraffin (or other inert cream gel). Then this stick(s) is inserted into the gravid uterus with the help of the dilator. The stick(s) is inserted into the uterus in such a way that the stick(s) crosses the internal Os of the cervices. The dilator is used to place the stick(s) safely into the uterus so that the stick(s) reaches its place of action without getting broken. The stick starts showing its effect normally not before 8-10 hours. But in some rear cases the proposed stick gives desired outcome within 2-3 hours. It initiates labor pain and provide normal contraction to the gravid uterus to help its dilution. For normal pregnancy case, once labor pain starts and the uterus gets one-fourth dilution, the stick is removed so that the normal delivery can occur and the uterus can get complete evacuation. In abnormal delivery cases, especially in case of intra uterine death of fetus/baby, there is no need of removal of stick(s) from the uterus because there is no fear of harm to the baby. In some cases these uterine stimulant sticks show their effect after 20-24 hours. In cases of uterine complications, other than normal pregnancy and normal delivery, more than one stick are applied, or single uterine stimulant stick with high power medicine content can be prescribed. Some times application of more than one sticks are applied simultaneously. Such direct application of stick (s to the uterus) is not at all painful or harmful to the woman under treatment; even she does not feel any trouble in movement and in release of urine.

3.4. Precautions in the Application of These Sticks:

A uterine stimulant drug can be considered as a very important life saving drug in very crucial stages of patients (as well as fetus/child), such as labor related cases; matters of uterine contractions following a miscarriage; abortion; hemorrhage following childbirth or abortion. Therefore it is very much relevant to consider certain facts like indications, contra indications and side effects for such important medicine.

Indications:
  Intra uterine death
  Mal-formed baby
  Poor contraction
  Hydatid Mole
  To avoid Caesarian section.

Contra Indications:
  Transver lie
  Placenta Previa
  Sever Bleeding
  Cephalo Pelvic Disproportion
  High Blood Pressure It is important to establish a clear baseline of vital signs before a woman is given proposed uterine stimulant medicine. Consistent reevaluation and documentation of vital signs permit faster recognition of an abnormal change in a woman's condition. Though the indications and contra indications for proposed medicine are mentioned above, the medicine and its method of administration are found very safe and produce hundred percent desired results in its clinical trials. Condition of women under treatment needs proper monitoring, especially for symptoms of contra indications and it is not advisable to apply proposed uterine stimulant stick on patients showing such symptoms, unless very much needed.

3.5. Side Effects of Proposed Uterine Stimulant Sticks:

The proposed medicine and the method of its application are found hundred percent safe and result producing. In very few cases (in less than 2% cases) patients have shown side effects, like vomiting and high temperature (fever). To avoid such side effects and any further complications, it is advisable to give counter medicines like antibody and anti-vomiting pill/injection etc. Apart from these two types of side effects—vomiting and high temperature in less than 2% patients, not any other symptoms like headache, nausea, diarrhea, tachycardia, chills, sweating, hypertension, hypotension, increased incidence of uterine hyper stimulation and potential for uterine rupture etc. are observed. Therefore the proposed uterine stimulant stick is much more safe, side effect free and normal contraction initiating medicine as compare to other conventionally available such stimulants.

The proposed uterine stimulant sticks can be prepared very economically and its active life expires at least after one year from the date of its manufacture. It can be kept safely wrapped in any suitable cover in a dry and cold place. It is advisable to keep these sticks from the reach of children as they contain toxic compounds like blue vitriol. Their application is also very easy and safe. Therefore such medicine is very important to check pregnancy and childbirth related deaths. Such medicine can serve the purpose of an economical and safe drug in its category, especially in developing countries and in under developed regions of the world, where malnutrition is a very frequent phenomenon associated with ladies community.

3.6. Some Exemplary Cases Explaining the Use of Proposed Uterine Stimulant Sticks are Mentioned Below:

(i) In normal cases of pregnancy and delivery: A healthy woman undergoing normal pregnancy is treated with the proposed uterine stimulant stick to result sufficient contraction and normal delivery. Similarly, in case a woman does not feel labor pain on the expected period, she can be treated with the proposed stick to start labor pain followed by normal delivery In these type of cases, under supervision of doctor, only one uterine stimulant stick is inserted into the gravid uterus of the woman undergoing delivery. In such cases one uterine stimulant stick is sufficient in carrying out its purpose. The stick is inserted into the uterus with the help of the dilator in such a manner that the stick crosses the internal Os of the cervices. The stick is allowed to remain in the uterus until its one-fourth dilution. This condition is normally observed after 8-10 hours. In exceptionally few cases, one-fourth dilution is observed within 3-4 hours. After reaching this condition of uterus, the stick is removed carefully, so that the baby under birth does not get hurt. During this whole period of treatment with the proposed uterine stimulant stick, the peasant is kept under observation for side effects. In very few cases (in less than 2% cases) patients have shown side effects like vomiting, and high temperature (fever). To avoid such side effects and any further complications, it is advisable to give counter medicines like antibody and anti-vomiting pill/injection etc.

(ii) In case of abnormal pregnancy and abnormal delivery cases: Abnormal pregnancy is a common problem, due to several reasons such as malnutrition, abnormal blood pressure, abnormal sugar level, low or high weight etc. Due to such abnormalities and other metabolisms of pregnant woman, the delivery date may get affected, reaches early or gets delayed. Some time the pregnant woman does not feel labor pain. Delay in delivery (even due to early delivery too) can cause danger to the life of the baby inside the womb. If a lady has case history of cesarean, there is always a possibility of insufficient contraction in second/next delivery. In case of intra uterine death, abortion is needed because no normal contraction is possible, until some external medical/surgical support is provided to the peasant. Therefore in all such cases mentioned above, the proposed uterine stimulant stick works excellent and solves all complications without creating any cesarean treatment. In abnormal delivery cases two uterine stimulant sticks are often applied. For intra uterine deaths, some times two to three uterine stimulant sticks are applied. In cases of intra uterine death within 4 months of pregnancy, two sticks are placed into the gravid uterus to expel out dead fetus without cesarean. Similarly, in those intra uterine deaths where the pregnancy continued for more than five months, two uterine stimulant sticks are preferably prescribed. In case of intra uterine death between 4 to 5 months of pregnancy, three uterine stimulant sticks are applied. These sticks act efficiently in the gravid uterus as they carry sufficiently calculated amount of active uterine stimulant medicine. In spite of multiple sticks, a single one containing sufficiently high medicine content can also be applied. In those cases of delivery where a baby takes birth, the uterine stimulant stick(s) should be removed from the uterus so that it can't harm the baby. In cases of intra uterine death, there is no need of removal of the stick(s), as there is no fear of harm to the dead fetus/baby. The stick(s) is helpful in expelling the baby/fetus and completely evacuation of the uterus. Through out the treatment, the peasant is strictly observed for any odd development. To check the side effects of the proposed uterine stimulant medicine, it is advisable to give counter medicines like antibody and anti-vomiting pill/injection etc. Apart from these two types of side effects—vomiting and high temperature in less than 2% patients, not any other symptoms like headache, nausea, diarrhea, tachycardia, chills, sweating, hypertension, hypotension, increased incidence of uterine hyper stimulation and potential for uterine rupture etc. are observed. Therefore the proposed uterine stimulant stick is much more safe, side effect free and normal contraction initiating medicine as compare to other conventionally available such stimulants.

We claim:

1. A uterine stimulant stick comprising a round-surfaced inert stick tightly wrapped with a first layer of absorbent material and having Icthomal, Oak milk and powdered Blue Vitriol absorbed thereon, the round-surfaced inert stick having a first end, a second end and a middle and the first layer of absorbent material covers the first end, the second end and the middle, and a second layer of absorbent material covers the first end.

2. The uterine stimulant stick of claim 1, wherein the Icthomal, the Oak milk and the powdered Blue Vitriol are at a ratio of 50:50:1 to one another.

3. The uterine stimulant stick of claim 1, wherein the uterine stimulant stick has 500 mg of the Icthomal, 500 mg of the Oak milk and 10 mg of the powdered Blue Vitriol absorbed thereon.

4. The uterine stimulant stick of claim 1, wherein the first layer of absorbent material is cotton.

5. The uterine stimulant stick of claim 1, wherein the second layer of absorbent material is cotton.

6. The uterine stimulant stick of claim 5, wherein the first layer of absorbent material is cotton and the uterine stimulant stick has 500 mg of the Icthomal, 500 mg of the Oak milk and 10 mg of the powdered Blue Vitriol absorbed thereon.

7. The uterine stimulant stick of claim 1, wherein the Icthomal, the Oak milk, and the powdered Blue Vitriol are at a ratio of 1:1:0.1 gm.

* * * * *